US006479287B1

(12) United States Patent
Reichert et al.

(10) Patent No.: US 6,479,287 B1
(45) Date of Patent: Nov. 12, 2002

(54) METHOD FOR TRANSFORMATION OF COTTON AND ORGANOGENIC REGENERATION

(75) Inventors: Nancy A. Reichert, Starkville, MS (US); Teong-Kwee Lim, Johor (MY); Margaret M. Young, Falmouth (JM)

(73) Assignee: Mississippi State University, Mississippi State, MS (US)

(*) Notice: Subject to any disclaimer, the term of this patent is extended or adjusted under 35 U.S.C. 154(b) by 0 days.

(21) Appl. No.: 09/562,193

(22) Filed: May 1, 2000

(51) Int. Cl.$^7$ ................................................. C12N 5/02
(52) U.S. Cl. .................... 435/427; 435/430; 435/430.1; 435/431
(58) Field of Search ................................ 435/427, 430, 435/430.1, 431

(56) References Cited

U.S. PATENT DOCUMENTS

| | | | |
|---|---|---|---|
| 5,159,135 A | 10/1992 | Umbeck | 800/205 |
| 5,244,802 A | 9/1993 | Rangan | 435/240.5 |
| 5,495,070 A | 2/1996 | John | 800/205 |
| 6,242,257 B1 * | 6/2001 | Tuli | 435/427 |

OTHER PUBLICATIONS

Abstract, Srivastava et al, Acta Hort. (289) p. 263–264 1991.*
Dodds et al, Experiments in Plant Tissue Culture, p. 36–38, 1985.*
Bidney, D., C. Scelonge, J. Martich, M. Burrus, L. Sims, and G. Huffman. 1992. Microprojectile bombardment of plant tissue increases transformation frequency by *Agrobacterium tumefaciens*. Plant Mol. Biol. 18:301–313.
Chi, G., D. G. Barfield, G. Sim, and E. Pua. 1990. Effect of AgNO$_3$ and aminoethoxyvinylglycine on in vitro shoot and root organogenesis from seeding explants of recalcitrant Brassica genotypes. Plant Cell Rpt. 9:195–198.
Chlan, C.A., J. Lin, J.W. Cary, and T.E. Cleveland. 1995. A Procedure for Biolistic Transformation and Regeneration of Transgenic Cotton from Meristematic Tissue. Plant Mol. Biol. Rptr. 13(1):31–37.
Dixon, R. A. 1985. Isolation and maintenance of callus and cell suspension cultures. In Plant Cell Culture: A Practical Approach, R. A. Dixon, ed., IRL Press, Washington, D.C., pp. 1–20.
Finer, J.J., and M.D. McMullen. 1990. Transformation of cotton (*Gossypium hirsutum L.*) via particle bombardment. Plant Cell Rpt. 8:586–589.
Firoozabady, E., D.L. DeBoer, D.J. Merlo, E.L. Halk, L.N. Amerson, K.E. Rashka, and E.E. Murray. 1987. Transformation of cotton (*Gossypium hirsutum L.*) by *Agroacterium tumefaciens* and regeneration of transgenic plants. Plant Mol. Biol. 10:105–116.

Firoozabady, E., and D. L. DeBoer. 1993. Plant regeneration via somatic embryogenesis in many cultivars of cotton (*Gossypium hirsutum L.*). In Vitro Cell. Dev. Biol. 29P:166–173.
Hyde, C. L., and G. C. Phillips. 1996. Silver nitrate promotes shoot development and plant regeneration of chile pepper (*Capsicum annuum L.*) via organogenesis. In Vitro Cell. Dev. Biol. 32P:72–80.
Ishida, Y., H. Saito, S. Ohta, Y. Hiei, T. Komari, and T. Kumashiro. 1996. High efficiency transformation of maize (*Zea mays L.*) mediated by *Agrobacterium tumefaciens*. Nature Biotechnology vol. 14:745–750.
Jefferson, R. A. 1987. Assaying Chimeric Genes in Plants: The GUS Gene Fusion System. Plant Mol. Biol. Rptr. vol. 5:387–405.
McCabe, D.E., and B.J. Martinell. 1993. Transformation of Elite Cotton Cultivars via Particle Bombardment of Meristems. Bio/Technology vol. 11:596–598.
Murashige, T., and F. Skoog. 1962. A Revised Medium for Rapid Growth and Bio Assay with Tobacco Tissue Cultures. Physiol. Plant. vol. 15:473–497.
Nitsch, J.P., and C. Nitsch. 1969. Haploid Plants from Pollen Grains. Science vol. 163:85–87.
Peeters, M. C., K. Willems, and R. Swennen. 1994, Protoplast–to–plant regeneration in cotton (*Gossypium hirsutum L.* cv. Coker 312) using feeder layers. Plant Cell Rpt. 13:208–211.
Phillips, R. L., S. M. Kaeppler, and P. Olhoft. 1994, Genetic instability of plant tissue cultures: Breakdown of normal controls. Proc. Natl. Acad. Sci. USA. vol. 91:5222–5226.
Pua, E., G. Sim, G. Chi, and L. Kong, 1996. Synergistic effect of ethylene inhibitors and putrescine on shoot regeneration from hypocotyl explants of Chinese radish (*Raphanus sativus L.* var. *Longipinnatus Bailey*) in vitro. Plant Cell. Rpt. 15:685–690.
Purnhauser, L., P. Medgyesy, M. Czako, P.J. Dix, and L. Marton. 1987. Stimulation of shoot regenration in *Triticum aestivum* and *Nicotiana plumbaginifolia* Viv. tissue cultures using the ethylene inhibitor AgNO$_3$. Plant Cell Rpt. 6:1–4.

(List continued on next page.)

Primary Examiner—Bruce R. Campell
Assistant Examiner—Anne Marie Grunberg
(74) Attorney, Agent, or Firm—Piper Rudnick LLP; Steven B. Kelber

(57) ABSTRACT

Protocols for organogenic regeneration of cotton are provided, which makes the in vitro regeneration of mature fertile plants in a reduced amount of time possible. Seedlings are the basis for monocotyl or hypocotyl explants which are transferred from the germination medium to a shoot initiation medium which comprises AgNO$_3$. These explants, prior to shoot initiation, may be transformed with exogenous DNA, either through inoculation with an Agorbacterium agent such as A. tumefaciens, or through biolistic bombardment of the explants with microprojectiles having the exogenous DNA adsorbed onto their surface.

6 Claims, No Drawings

OTHER PUBLICATIONS

Rajasekaran, K., J.W. Grula, R.L. Hudspeth, S. Pofelis, and D.M. Anderson. 1996. Herbicide–resistant Acala and Coker cottons transformed with a native gene encoding mutant forms of acetohydroxyacid synthase. Mol. breed. 2:307–319.

Shoemaker, R.C., L.J. Couche, and D.W. Galbraith. 1986. Characterization of somatic embryogenesis and plant regeneration in cotton (*Gossypium hirsutum L.*). Plant Cell Rpt. 3:178–181.

Svab, Z., and P. Maliga. 1993. High–frequency plastid transformation in tobacco by selection for a chimeric *aadA* gene. Proc. Natl. Acad. Sci. USA vol. 90:913–917.

Umbeck, P., G. Johnson, K. Barton, and W. Swain. 1987. Genetically transformed cotton (*Gossypium hirsutum L.*) plants. Bio/technology vol. 5:263–266.

\* cited by examiner

METHOD FOR TRANSFORMATION OF COTTON AND ORGANOGENIC REGENERATION

BACKGROUND OF THE INVENTION

Field of the Invention

This invention pertains to the transformation, on the one hand, and organogenic regeneration, on the other hand, of cotton plants, a commercially important crop. Both nuclear and plastid transformation are embraced.

DISCUSSION OF THE BACKGROUND

Cotton has been traditionally recalcitrant to regeneration in vitro. Most regeneration successes have entailed the sole use of Coker lines which respond in. tissue culture but are not agronomically important (Chlan et al., 1995; Firoozabady et al., 1987; Peeters et al., 1994; Shoemaker et al., 1986; Umbeck et al., 1987). Most (if not all) developed regeneration protocols entail the production of embryogenic callus from seedling explants such as cotyledon and hypocotyl sections, followed by the formation of somatic embryos with subsequent germination and conversion into mature cotton plants (Firoozabady and DeBoer, 1993; Firoozabady et al., 1987; Peeters et al., 1994; Rajasekaran et al., 1996; Shoemaker et al., 1986; Umbeck et al., 1987; U.S. Pat. Nos. 5,159,135, and 5,244,802). This type of regeneration procedure could take up to 40 weeks and could produce unwanted mutations due to the presence of a prolonged callus phase prior to regeneration.

Cotton tissues have been successfully transformed with A. tumefaciens prior to generation of embryogenic callus used in regeneration (Firoozabady et al., 1987; Rajasekaran et al., 1996; Umbeck et al., 1987). Cotton has also been transformed via biolistics with tissues also undergoing regeneration via somatic embryogenesis (Rajasekaran et al., 1996). A few protocols have recently utilized intact meristem-tips as targets in biolistics-based transformations with regeneration occurring via a more direct organogenic route (Chlan et al., 1995; Finer and McMullen, 1990; McCabe and Marinelli, 1993). Although this has overcome some regeneration obstacles, it is technically demanding. Due to their extremely small size (<1.0 mm), the meristem-tips have to be excised with the aid of a dissecting microscope and once isolated, need to be utilized shortly thereafter.

Accordingly, it remains an object of those of skill in the art to develop a method for regeneration of cotton, in vitro, with an eye to obtaining genetic variation providing desirable qualities. In particular, it is an object of those of skill in the art to obtain a method for transforming plant tissues with exogenous DNA, or obtaining mutations of endogenous DNA, and regenerating the tissues containing these DNA alterations and additions into mature, fertile plants.

SUMMARY OF THE INVENTION

The objects set forth above, and others, are obtained by the invention summarized below, and detailed on the following pages. Our regeneration method utilizes seedling explants such as hypocotyl as in the somatic embryogenic method, but regeneration is via organogenesis and does not involve the lengthy callus intermediate step. Regeneration therefore can be achieved in a shorter period of time and with a less likelihood of inducing unwanted mutations during the regeneration process. This organogenic regeneration protocol also has been demonstrated to work on commercially important cultivars and, therefore, would be more useful in transformation protocols. This regeneration method can be successfully combined with either type of transformation system, nuclear or plastid.

Seeds of commercial cultivars are surface disinfected and germinated aseptically on media. Seedling hypocotyl explants are placed on media (MS-based, Murashige and Skoog, 1962; NH-based, Nitsch and Nitsch, 1969), containing plant growth regulators (PGRs) 1-naphthaleneacetic acid (NAA) and thidiazuron (TDZ). Silver nitrate is also added to the media.

For transformation, explants are placed on shoot initiation media prior to bombardment and/or incubated in A. tumefaciens bacterial cultures depending on the type of transformation desired. Tissues are then analyzed for the presence and integration of foreign DNA by various methods. Transgenic plants are regenerated via the above process on selective media. The subsequent progeny are also analyzed for patterns of foreign DNA inheritance.

DETAILED DESCRIPTION OF THE INVENTION

This invention pertains to methods of regeneration of cotton, using organogenesis, coupled with methods of transformation of this important commercial crop, which can be used to introduce exogenous DNA to provide more desirable species, which can be regenerated using the regeneration protocols to provide mature, fertile plants which breed true (pass on the transformed or exogenous DNA and the traits encoded thereby).

The detailed discussion below describes cotton regeneration, together with a method for transformation.

It is important to note that cotton can be transformed using either Agrobacterium, such as A. tumefaciens coupled with wounding, or through biolistic bombardment. In connection with biolistic bombardment, both nuclear and plastid DNA can be targeted. Where using DNA for introduction into plastids, for transformation, smaller microprojectiles (0.4–0.7 microns verses 1.0–1.7 microns) may be advantageously employed, and DNA containing chimeric genes that can be expressed in plastids are utilized. One example, not intended to be limiting, of this type of vector is pZS 197 containing a chimeric aadA gene which confers resistance to spectinomycin (Svab & Maliga, 1993). A similar plastid expression vector supplied by Dr. Hans-Ulrich Koop, Botanisches Institut, Germany, was made available. Use of vectors containing the aadA gene enables the use of non-lethal selection to identify cells in plants containing transformed plastids. After bombardment, tissues would be grown on shoot initiation media containing spectinomycin and/or streptomycin but otherwise conducted as described herein below.

Transformation and Regeneration of Commercial Cotton Varieties

This method involves the following:
(1) surface sterilization and germination of seeds in vitro
(2) excision of tissues such as hypocotyl explants for use in transformation and regeneration
(3) introduction of DNA via Agrobacterium tumefaciens and/or biolistics
(4) selection of transformed tissues in the presence of antibiotic or herbicide to allow selective growth of transformed shoots (antibiotic or herbicide resistance gene is part of introduced DNA)
(5) growth of transformed shoots with subsequent rooting
Detailed Protocols:

(1) Seeds[a] are surface disinfected in a bleach solution (25%, v/v) containing 0.5% SDS (detergent) for 20 min., then rinsed 4 times with sterile distilled water. Seeds are placed in/on Nitsch & Nitsch (NH-based) or Murashige & Skoog (MS-based) media (cefotaxime may be added) for 1–2 weeks to allow germination.

(2) Explants (hypocotyl) are excised and placed on shoot initiation media.

(3) DNA is introduced with A. tumefaciens via a modified protocol of those already reported. DNA was successfully delivered into cotton Coker lines (commercially unimportant) by Umbeck et al. (1987; hypocotyl sections), Firoozabady et al. (1987; cotyledon sections), and Rajasekaran et al. (1996; both explants)[c].

Introduction of DNA via the PDS-1000/He apparatus utilizes a modified protocol of those developed and currently used in N. Reichert's lab on other crops. Rajasekaran et al. (1996) successfully introduced DNA into embryogenic cotton lines (Coker and Acala) via the PDS-1000/He[d]. Multiple bombardments may increase transformation efficiencies, as has been demonstrated in cotton (Rajasekaran et al., 1996).

DNA introduction via a combination of biolistics and A. tumefaciens may also enhance the recovery of transformed cotton tissues. In other plant species, this has been demonstrated to increase A. tumefaciens transformation efficiencies due to enhanced wounding (Bidney et al., 1992[c]).

(4) Selection systems currently in use include the use of geneticin (G418) and kanamycin (chimeric nptII gene), phosphinothriein (chimeric bar gene) and hygromycin (chimeric hph gene) for selection of transformants.

(5) Adventitious shoots emerge from tissues containing introduced DNA by growth on media containing a selection agent as discussed above. Transformed shoots that arise are cut and placed on a rooting medium.

Notes:
a. Commercial cotton varieties such as Deltapine 50, Stoneville 474 have been used.
b. Previously, researchers primarily introduced DNA into commercially unimportant lines, and regeneration (Coker and non-Coker lines) was through somatic embryogenesis which entailed a protracted culture period [up to 24 weeks to generate embryogenic callus (Rajasekaran et al., 1996)]. This callus was then transferred to a second medium for production of somatic embryos, which were subsequently transferred to a third medium to achieve germination. Regeneration via adventive shoot organogenesis as described works on commercially important varieties and shortens the time it takes to produce transgenic cotton plants. In addition, since a prolonged callus phase will be avoided, there should be less chances for production of mutated cotton plants due to somaclonal variation.
c. The tissues Rajasekaran et al. (1996) used in bombardments with the PDS1000/He apparatus were embryogenic callus lines initiated from seedling explants. Regeneration then entailed development of somatic embryos from this callus (U.S. Pat. No. 5,244,802). As stated above, maintenance of cotton tissues in the callus phase for prolonged periods of time will increase the prevalence of mutations in cotton regenerants. d. Bidney, D., C. Scelonge, J. Martich, M. Burrus, L. Sims, and G. Huffman. 1992. Microprojectile bombardment of plant tissues increases transformation frequency by *Agrobacterium tumefaciens*. Plant Mol. Biol. 18:301–313.

Regeneration of Cotton

Shoot Regeneration from Hypocotyl Sections of Cotton

All culture stages were incubated under a 16 h. photoperiod at room temperature.

Seed Sterilization and Germination:

Cotton seeds were soaked for 5 minutes in 70% ethanol, then surface sterilized for 25 minutes using 25% commercial bleach and 0.5% sodium dodecyl sulfate (SDS) on a shaker (200 rpm). The seeds were rinsed 3 times with sterile deionized double distilled water and placed on a growth maintenance medium (GMS) GMSC [MS basal salts, 1.0 mg/l thiamine-HCL, 0.5 mg/l pyridoxine-HCL, 0.5 mg/l nicotinic acid, 100 mg/l myo-inositol, 30 g/l glucose, 0.8 g/l phytagar, pH 5.8; plus 500 mg/l cefotaxime (for bacterial contamination)] for one week. Germinated seeds (with at least the radicle emergent) were then placed in liquid GMSC (no phytagar) for an additional week. After 1 week in liquid medium, the cotyledons and shoot tips were clearly visible. Hypocotyl sections (one per seedling) were then excised with the acropetal cut made just below the cotyledonary nodes (the cut was made on a line that is clearly visible on the explants). The basipetal cut was made 1.0 cm below the initial cut Shoot Initiation, Elongation, and Rooting Hypocotyl sections were placed horizontally on shoot initiation medium (GA). Explants were maintained for 6 weeks on this medium. Shoot primordia were visible on the acropetal ends of hypocotyl sections after 2 weeks. After 6 weeks, leaves were clearly visible. Shoot initiation has been observed in 7 commercial cultivars (Deltapine 50, Stoneville 474, Deltapine 5111, Tx 121, Suregrow 125, Fibermax 819, and Paymaster 1215) and 3 breeding lines, and the response ranged from 20–73% (percentage explants capable of initiating shoots per cultivar).

At the end of 6 weeks, the upper 1.0 cm portion of the acropetal ends were excised and placed on shoot elongation medium (GB). Cultures were maintained on this medium for an additional 6 weeks. Rooting can occur in this medium. Up to 5 elongated shoots per explant have been generated.

Shoots with a defined shoot pole were excised from shoot clumps for rooting on GC. Rooting may take up to 6 weeks. Plants can be successfully acclimatized in 2 weeks.

GA: semi-solid GMS plus an auxin like NAA (0.1–3.0 mg/l), a cytokinin like TDZ, or BA plus kinetin (0.1–2.5 mg/l) and 1–50 mg/l silver nitrate GB: semi-solid GMS plus an auxin like NAA (0.1–1.0 mg/l), a cytokinin like kinetin plus BA (0.1–1.0 mg/l each), gibberellic acid like $GA_3$ (0.1–1.0 mg/l) and activated charcoal (0.1–2.0 g/l)

GC: semi-solid GMS plus an auxin like NAA or IBA (0.1–1.0 mg/l) and activated charcoal (0.1–2.0 g/l)

Histological Analyses:

Apical portions were excised from newly cut, 2, and 4 week old explants. Observations on explants that have been newly cut indicated that intact cotyledonary nodes were not present. After 2 weeks, the explant had increased in width and numerous shoot meristems (densely stained) were clearly visible, particularly in the central portion of the explant. These shoot meristems arose from the parenchyma cells of the central pith. Leaf primordia were forming around the young shoot tip. No vascular tissues were connected to these early shoot meristems, although they were visible in the original lower pith region of the explant.

After 4 weeks, the explant had increased tremendously in width. Well-defined leaf primordia and shoot tips were visible. The internode region of each shoot had started to elongate with its own epidermal and pith layer (differentiation into plant tissues was occurring). Vascular tissues were beginning to be formed in the internode region.

Dose Response Studies:

The effect of the aminoglycosides kanamycin and geneticin on cotton shoot initiation were investigated.

Kanamycin, at concentrations of 0.0, 50, 100, 150 and 200 mg/l, and geneticin at 0.0, 5.0, 10, 15 and 20 mg/l, were incorporated in medium GA. The experiment consisted of 3 replicate plates/treatment and 4 explants/replicate plates using the cultivar Deltapine 50. Results after 1 month indicated that a kanamycin concentration of 50 mg/l was sufficient to inhibit shoot initiation. A geneticin concentration up to 20 mg/l was not inhibitory to shoot initiation.

Biolistics-based Bombardments

Factors affecting GUS transient expression were optimized using cultivars Deltapine 50 and Stoneville 474. The PDS-1000/He device was utilized using a vacuum pressure of 25–26 mm Hg. There were 20 explants/plate and each plate was bombarded once or twice with 750 $\mu$g–10 microprojectiles. GUS transient expression (nine randomly selected explants per cultivar) was assayed histochemically, 3 days post-bombardment. Optimized factors were: pressure of 1350 psi, 3/8 in gap distance, 7.5 cm target distance, 2–20 $\mu$g DNA (pBI121) and a preculture time of 1 day.

Seed germination for two weeks

[Surface sterilization then placement on GMSC for 1 week. Seedling transfer to liquid GMSC for 1 week]

Shoot initiation on GA for 6 weeks

[Excised hypocotyl sections are placed horizontally on medium]

Shoot elongation/rooting on GB for 6 weeks

↓

Root formation on GC for 6 weeks

↓

Acclimatization of plants for 2 weeks

Schematic diagram of shoot regeneration from hypocotyl sections of cotton.

References

1. Bidney, D., C. Scelonge, J. Martich, M. Burrus, L. Sims, and G. Huffman. 1992. Microprojectile bombardment of plant tissues increases transformation frequency by *Agrobacterium tumefaciens*. Plant Mol. Biol. 18:301–313.
2. Chi, G., D. G. Barfield, G. Sim, and E. Pua. 1990. Effect of AgNO$_3$ and aminoethoxyvinylglycine on in vitro shoot and root organogenesis from seedling explants of recalcitrant *Brassica* genotypes. Plant Cell Rpt. 9:195–198.
3. Chlan, C. A., J. Lin, J. W. Cary, and T. E. Cleveland. 1995. A Procedure for Biolistic Transformation and Regeneration of Transgenic Cotton from Meristematic Tissue. Plant Mol. Biol. Rptr. 13(1):31–37.
4. Dixon, R. A. 1985. Isolation and maintenance of callus and cell suspension cultures. In Plant Cell Culture: A Practical Approach, R. A. Dixon, ed., IRL Press, Washington, D.C., pp. 1–20.
5. Finer, J. J., and M. D. McMullen. 1990. Transformation of cotton (*Gossypium hirsutum L.*) via particle bombardment. Plant Cell Rpt. 8:586–589.
6. Firoozabady, E., D. L. DeBoer, D. J. Merlo, E. L. Halk, L. N. Amerson, K. E. Rashka, and E. E. Murray. 1987. Transformation of cotton (*Gossypium hirsutum L.*) by *Agrobacterium tumefaciens* and regeneration of transgenic plants. Plant Mol. Biol. 10:105–116.
7. Firoozabady, E., and D. L. DeBoer. 1993. Plant regeneration via somatic embryogenesis in many cultivars of cotton (*Gossypium hirsutum L.*). In Vitro Cell. Dev. Biol. 29P:166–173.
8. Hyde, C. L., and G. C. Phillips. 1996. Silver nitrate promotes shoot development and plant regeneration of chile pepper (*Capsicum annuum L.*) via organogenesis. In Vitro Cell. Dev. Biol. 32P:72–80.
9. Ishida, Y., H. Saito, S. Ohta, Y. Hiei, T. Komari, and T. Kumashiro. 1996. High efficiency transformation of maize (*Zea mays L.*) mediated by *Agrobacterium tumefaciens*. Nature Biotechnology Vol. 14:745–750.
10. Jefferson, R. A. 1987. Assaying Chimeric Genes in Plants: The GUS Gene Fusion System. Plant. Mol. Biol. Rptr. Vol. 5:387–405.
11. McCabe, D. E., and B. J. Martinell. 1993. Transformation of elite cotton cultivars via particle bombardment of meristems. Bio/Technology Vol. 11:596–598.
12. Murashige, T., and F. Skoog. 1962. A Revised Medium for Rapid Growth and Bio Assay with Tobacco Tissue Cultures. Physiol. Plant. Vol. 15:473–497.
13. Nitsch, J. P., and C. Nitsch. 1969. Haploid Plants from Pollen Grains. Science Vol. 163:85–87.
14. Peeters, M. C., K. Willems, and R. Swennen. 1994. Protoplast-to-plant regeneration in cotton (*Gossypium hirsutum L.* cv. Coker 312) using feeder layers. Plant Cell Rpt. 13:208–211.
15. Phillips, R. L., S. M. Kaeppler, and P. Olhoft. 1994. Genetic instability of plant tissue cultures: Breakdown of normal controls. Proc. Natl. Acad. Sci. USA. Vol. 91:5222–5226.
16. Pua, E., G. Sim, G. Chi, and L. Kong, 1996. Synergistic effect of ethylene inhibitors and putrescine on shoot regeneration from hypocotyl explants of Chinese radish (*Raphanus sativus L.* var. *Longipinnatus* Bailey) in vitro. Plant Cell. Rpt. 15:685–690.
17. Rajasekaran, K., J. W. Grula, R. L. Hudspeth, S. Pofelis, and D. M. Anderson. 1996. Herbicide-resistant Acala and Coker cottons transformed with a native gene encoding mutant forms of acetohydroxyacid synthase. Mol. Breed. 2:307–319.
18. Purnhauser, L., P. Medgyesy, M. Czako, P. J. Dix, and L. Marton. 1987. Stimulation of shoot regeneration in *Triticum aestivum* and *Nicotiana plumbaginifolia* Viv. tissue cultures using the ethylene inhibitor AgNO$_3$. Plant Cell Rpt. 6:1–4.
19. Shoemaker, R. C., L. J. Couche, and D. W. Galbraith. 1986. Characterization of somatic embryogenesis and plant regeneration in cotton (*Gossypium hirsutum L.*). Plant Cell Rpt. 3:178–181.
20. Svab, Z., and P. Maliga. 1993. High-frequency plastid transformation in tobacco by selection for a chimeric aadA gene. Proc. Natl. Acad. Sci. USA Vol. 90:913–917.
21. Umbeck, P., G. Johnson, K. Barton, and W. Swain. 1987. Genetically transformed cotton (*Gossypium hirsutum L.*) plants. Bio/Technology Vol. 5:263–266.

What is claimed is:

1. A method of regenerating, in vitro, a mature fertile cotton plant through direct organogenesis, said method comprising:

excising an explant, which is a hypocotyl explant, maintaining said explant on a shoot initiation medium comprising thidiazuron until shoot formation on said explant is observed, transferring said shoot-bearing explant to one to two growth maintenance media until root formation is observed, indicating formation of a rooted plantlet, and planting said rooted plantlet and growing the same into a mature plant.

2. The method of claim 1, wherein said hypocotyl explant is obtained from a seedling which is obtained by sterilization of seeds of cotton and placing said sterilized seeds on a NH or MS growth medium.

3. The method of claim 2, wherein said NH or MS growth medium comprises a plant growth regulator selected from the group consisting of a cytokinin, an auxin and mixtures thereof.

4. The method of claim 3, wherein said cytokinin is thidiazuron (TDZ) and said auxin is 1-naphthaleneacetic acid (NAA).

5. The method of claim 1, wherein said shoot initiation medium comprises $AgNO_3$ in an amount up to 250 mg/l.

6. The method of claim 5, wherein said shoot initiation medium further comprises-naphthaleneacetic acid.

* * * * *

UNITED STATES PATENT AND TRADEMARK OFFICE
CERTIFICATE OF CORRECTION

PATENT NO. : 6,479,287 B1  Page 1 of 1
DATED : November 12, 2002
INVENTOR(S) : Nancy A. Reichert et al.

It is certified that error appears in the above-identified patent and that said Letters Patent is hereby corrected as shown below:

Title page,
Item [57], ABSTRACT,
Line 8, "Agorbacterium" should read -- Agrobacterium --.

Column 1,
Line 17, "in. tissue" should read -- in tissue --.

Column 3,
Line 13, "(1996; both explants)$^c$" should read -- (1996; both explants)$^b$ --.
Line 18, "PDS-1000/He$^d$" should read -- PDS-1000/He$^c$ --.
Line 25, "(Bidney et al., 1992$^c$)." should read -- (Bidney et al., 1992$^d$). --.
Line 28, "phosphinothriein" should read -- phosphinothricin --.
Lines 58-62, "d." should begin a new paragraph.
"in cotton regenerants. d. Bidney, D., C. Scelonge, J. Martich, M. Burrus, L. Sims, and G. Huffman. 1992. Microprojectile bombardment of plant tissues increases transformation frequency by *Agrobacterium tumefaciens*. Plant Mol. Biol. 18:301-313." should read
-- in cotton regenerants.
d. Bidney, D., C. Scelonge, J. Martich, M. Burrus, L. Sims, and G. Huffman. 1992. Microprojectile bombardment of plant tissues increases transformation frequency by *Agrobacterium tumefaciens*. Plant Mol. Biol. 18:301-313. --

Column 5,
Line 14, "$\mu$g-10" should read -- $\mu$g M-10 --.

Signed and Sealed this

Eighth Day of April, 2003

JAMES E. ROGAN
*Director of the United States Patent and Trademark Office*